United States Patent [19]

Beatty, III

[11] 4,387,710

[45] Jun. 14, 1983

[54] VENTILATED CAST STRUCTURE AND METHOD OF PRODUCING THE SAME

[76] Inventor: John C. Beatty, III, 2755 Parkridge Dr., Ann Arbor, Mich. 48103

[21] Appl. No.: 304,151

[22] Filed: Sep. 21, 1981

[51] Int. Cl.³ .............................................. A61F 5/04
[52] U.S. Cl. ................................................ 128/91 R
[58] Field of Search ............... 128/91 R, 83, 89, 87, 128/90

[56] References Cited

U.S. PATENT DOCUMENTS

| | | | |
|---|---|---|---|
| 2,998,921 | 9/1961 | Chester | 128/91 R X |
| 3,116,731 | 1/1964 | Baxter | 128/91 R |
| 3,998,220 | 12/1976 | Cleer, Jr. et al. | 128/91 R |

*Primary Examiner*—John D. Yasko
*Attorney, Agent, or Firm*—Bertram F. Claeboe

[57] ABSTRACT

A surgical structure for preventing skin irritation occasioned by confinement of a body part within a plaster cast featuring the provision intermediate the cast and body part of a loosely compacted fibrous layer communicating through a passage in the cast with a source of conditioned air controlled as to pressure, temperature and humidity and providing an air flow path adjacent the skin of the body part so that drying thereof is substantially avoided. A barrier layer is desirably located proximate the fibrous layer to prevent movement thereinto of cast material during the molding thereof. Connector means are provided from the air source through socket means embedded in the plaster cast and communicating with the loosely compacted fibrous layer.

12 Claims, 4 Drawing Figures

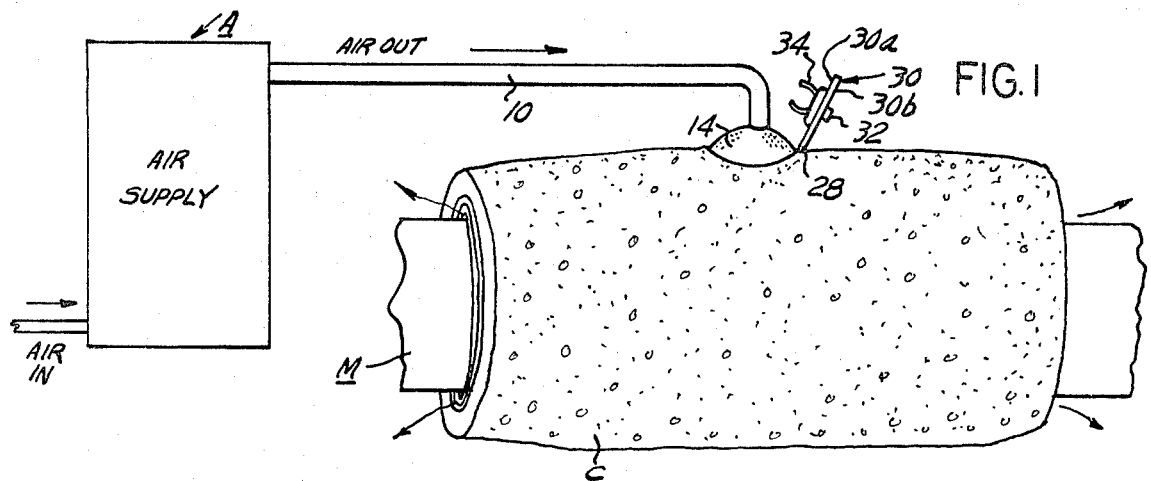
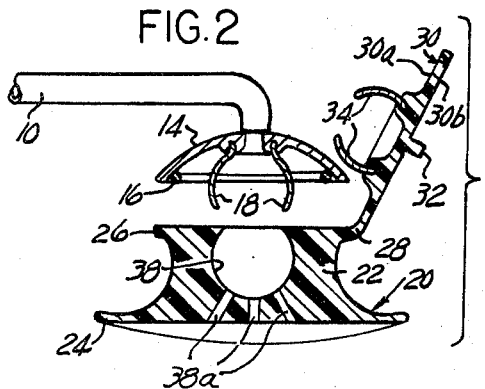
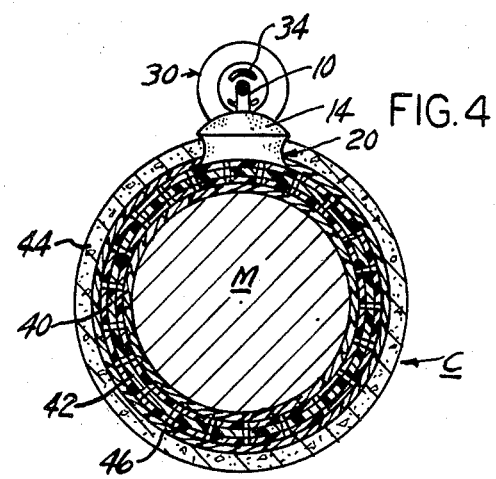
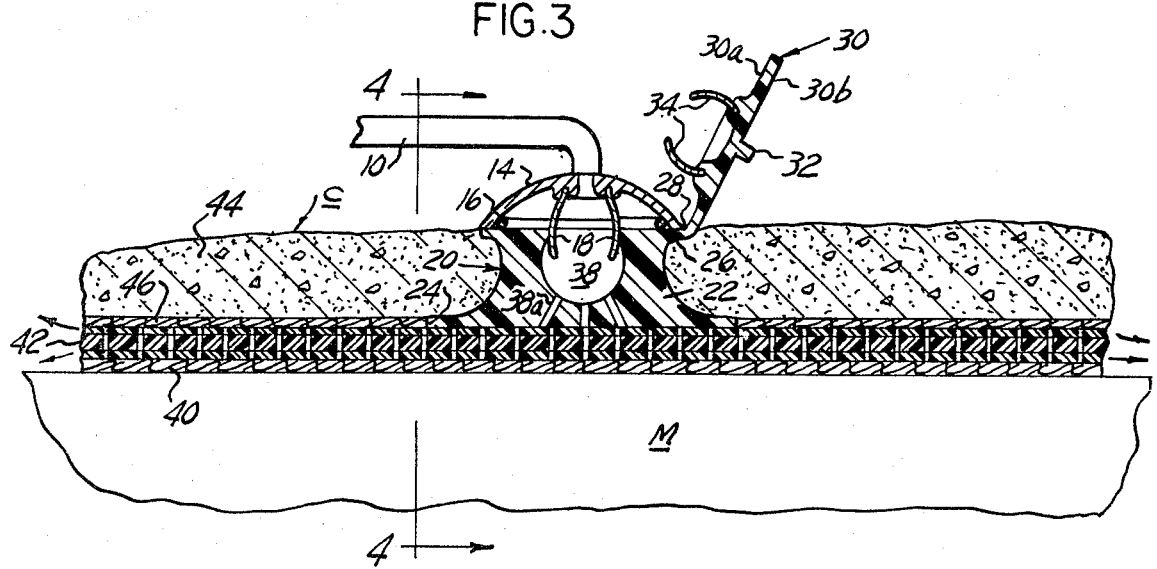

VENTILATED CAST STRUCTURE AND METHOD OF PRODUCING THE SAME

BACKGROUND OF THE INVENTION

It is known that when it is necessary to immobilize a human or animal limb by casting or related techniques, as may be required as a result of a bone fracture or like condition, the skin of the animal or human after a period of time becomes irritated and a desire or need to scratch that area develops. This condition is in a large measure due to the fact that there is little, if any, air circulation between the cast and skin surface, and to date no effective remedy for this has been found. Attempts to sprinkle powder between the cast and the fractured limb generally produces little relief from the itching, and it is known that upon occasion a person will attempt to force a foreign object between the skin and the cast for purposes of scratching the irritated area. The annoyance of skin irritation and the inability of the patient to do much about it is particularly aggravated when it is necessary to partially or totally restrain the patient. The itchy condition caused by skin irritation attributed to the absence of air circulation between the limb and cast is of course magnified when the environment is one of relatively high temperature and/or humidity.

SUMMARY OF THE INVENTION

It has been found by applicant that in the case of both animals and humans alike, discomfort, skin degradation, swelling and other symptoms caused by lack of air movement at the surface of the patient's skin can be markedly reduced if not entirely avoided by provision of a novel system of introducing controlled flow of conditioned air or other gaseous substances between the cast and the body part. Air from a suitable source is first filtered and then directed under controlled conditions of temperature, pressure and humidity to a ventilating assembly mounted by a cast structure surrounding the injured body part. The ventilating assembly preferably takes the form of a passaged socket member substantially entirely received within the cast, and during operation of the assembly communicating at one end with removable connector means. The socket member at its opposite end communicates with an air permeable layer and juxtaposed moisture impervious layer located between the body part and the cast, the former layer functioning as air distribution means and the latter layer as a barrier against ingress of plaster material during formation of the cast.

The air connector means and passaged socket member are adapted to mate in air-tight sealable relation during operation of the ventilation system, and when the system is not in use, the socket structure may be closed against the entry of foreign substances by a protective cover preferably permanently hingedly attached thereto.

BRIEF DESCRIPTION OF THE DRAWINGS

FIG. 1 is a diagrammatic side elevational view of the ventilation system of this invention;

FIG. 2 is a combined elevational view taken partially in section of connector and socket structures as during the assembly thereof;

FIG. 3 is an enlarged sectional view through the instant ventilation assembly in an operating mode with the connector member in position and the socket cover open; and FIG. 4 is a vertical sectional view taken substantially along the line IV—IV of FIG. 3, and illustrating the protective cover in a closed position relative to the socket structure.

DESCRIPTION OF THE PREFERRED EMBODIMENT

An air supply system effective for accomplishing the novel purposes of this invention is designated in FIG. 1 by the legend A and of course may take various forms. A suitable source of gas, which preferably is air, is an oil-free air compressor which may be of the rotary, centrifugal or reciprocating type. The compressor is normally of the electrically operated type, however, alternatively the source of air can be from a controlled central supply, such as is normally available in a hospital or other institution. Regardless of the source being used, and generally primarily for reasons of safety, the air should be supplied at generally less than about ten standard cubic feet per minute, and at a pressure not substantially exceeding approximately thirty pounds per square inch.

The air from the supply source is then preferably filtered to about fifty microns or less, and for this purpose the filter may be of the cartridge, flat, shaped or other known types. The filtered air is then dehumidified by any suitable means and substantially simultaneously chilled to not below about one degree C. at the evaporator side of the compressor, or alternatively, there may be utilized a thermal-electric cooler. It will be appreciated that as a further alternative the dehumidified air may be caused to pass through a coil structure located in cool water, ice water, snow or any other media capable of cooling the air to the desired temperature. Naturally, if the air passing from the filtration portion of this invention is of the requisite humidity and temperature values, this particular step can readily be omitted.

It is desirable that the temperature of the air at this point in the system be not substantially above fifty degrees C., and if it is necessary to slightly increase the temperature of the air subsequent to the dehumidification-cooling step, heat from the condensor side of the compressor may be utilized, or there can be employed the thermal-electric device earlier noted. Additionally, heat may be added by suitable electrical elements, or by passing the air through a coil which is immersed in any warm liquid.

It is further important in the present invention that the air supply unit designated generally by the legend A in FIG. 1 be portable and be of relatively quiet operation. More specifically, it is desirable that the unit A be housed in a compact, sound-insulated cabinet which may be hand-carried or rolled on wheels to the point of use. Relatively silent operation is important from the standpoint that the cast ventilating apparatus of this invention would be expected to be in operation during nocturnal hours, and further, may well be in use in proximity to the beds of other patients.

Referring now also to the other views of the drawings, conditioned air at the desired temperature, pressure, and humidity levels is directed by conduit means 10 which leads to sealing connector means 12 mounting a generally dome-like cap member 14. As appears in FIG. 2 of the drawings, the cap member 14 preferably carries on its underside sealing means 16 which may take the form of an elastomeric O-ring. The conduit means 10 desirably is in the form of plastic tubing having a generally right angle bend in the region where it joins the sealing connector member 12, for a purpose to be shortly described. The sealing connector member 12 may carry or be formed on its underside with a prong portion 18 desirably taking the form of a plurality of downwardly dependent curved fingers or tongs for removably attaching the connector member 12 to socket member 20.

The snap socket assembly 20, which preferably is molded of polymeric materials, is shaped to include a generally circular central body portion 22 connecting at one end with an outwardly flared skirt portion 24 which may be slightly upwardly turned as shown in FIG. 2. The body portion 22 of the snap socket assembly 20 is formed at its opposite end with a flared cap or collar portion 26 preferably integral with hinged-tether means 28 connecting with generally circular cover means 30 provided on top wall 30a with finger engaging tab means 32. On its bottom wall 30b the cap portion 30 is provided with snap prong means 34 for engagement within the upper collar portion 26 of the disposable snap socket assembly 20. An opening 36 in the socket assembly 20 communicates interiorly thereof with an air manifold 38 connecting with a plurality of air passages or branch connections 38a extending downwardly and outwardly through the flared skirt portion 24 of the socket member 20.

The sealing connector member 12, communicating by conduit means 10 with air supply A, is shown in FIG. 1 in an operating mode and thus in tight sealing relationship with the snap socket member 20 by means of the firm fitting contact between the cover member 14 and sealing ring 16 with the flanged collar 26 of the socket assembly 20, and more particularly, by the air-tight seal provided between the O-ring 16 or like means and the periphery of the collar flange 26 on the socket member 20.

The reusable sealing connector 12 makes a generally right angle connection relative to cast assembly C positioned on body part or member M, which may be any limb or other portion of a human or animal requiring immobilization for a rather prolonged period of time. It is significant to note that by provision of the generally right angle connection shown the conduit means 10 leading from the air supply A is normally disposed in rather close proximity to the cast assembly C and yet is not subject to kinking or tangling should the cast be moved a short distance relative to the conduit means 10, and also does not constitute interference with clothing on the person wearing the cast C. The sealing ring 16 on the underside of the connector cap portion 14 functions in the position shown in FIG. 1 as a pressure relief valve, and accordingly lifts or rises from its seat on the member 20 should an overpressure condition develop in the system, or if an attempt is made to connect the cast assembly C under conditions of an abnormally high pressure in the air supply system. A preferred structural material for the cap member 14 of the sealing connector assembly 12 is stainless steel mounting on its underside a sealing ring 16 desirably of silicone rubber. However, as an alternative, plastic or other elastomers may be used for the cap member 14.

The hinge means 28 connecting the cover member 30 to the snap socket assembly 20 is preferably formed integral therewith in order to minimize possible misplacement of the cover from the socket assembly. The tether hinge is preferably constructed of any moldable plastic material which permits repeated flexure, although as an alternative, the protective cover 30 could be of a metal-elastomer combination and completely removable from the socket assembly. As a further alternative, when uniting the sealing connector 12 with the socket member 20 pressure sensitive tape means may be employed therebetween.

Structural details of the novel cast assembly C of this invention are best shown in FIGS. 3 and 4, to which reference is now made. Located in intimate contact with the flesh of the body member M is a layer 40 of jersey or like woven material provided in sock form, as is known in the art, and which is pulled upon the injured body member by a medical attendant. Assuming for purposes of an example that the injured body part or member M is a fractured ankle, the jersey sock 40 would normally completely encase the calf portion of the leg.

Immediately adjacent the skin protector layer 40 of jersey or an equivalent material is an air distributor layer 42 forming an important part of the instant invention. This layer functions importantly in at least three major respects. First, it should have load bearing characteristics and be capable of resisting deformation under normal body pressures. Secondly, it should possess good flexibility so that it intimately conforms to the contours of the injured body member. Third, it should possess open passages, that is, be air permeable so that air may move or spread through it and hence out through the jersey layer 40 and from the cast assembly C in the manner shown by arrows. A presently preferred construction is of a sandwich type provided by a relatively coarse intermediate plastic grid having on its opposite surfaces in intimate juxtaposition therewith relatively finer mesh plastic screen cloth. The air distributor layer 42 as thus constructed is preferably an integral three-layer body, however, a suitable alternative construction may be provided by a woven plastic filament pad of the general texture found in abrasive-free cleansing pads. If the latter construction is selected, rather wide variations in density can be accepted, and it may be found by certain medical practioners that the air distributor layer 42 can completely take the place of the jersey layer 40, or in other words, the layer 42 can serve dual functions.

Superimposed upon the air distributor layer 42 and lying intermediate the latter layer 42 and the conventional plaster of Paris layer 44 is protective layer 46. Experience has indicated that the layer 46 juxtaposed between air distributor layer 42 and plaster cast layer 44 should possess at least three significant properties. First, it should be quite flexible, primarily for ease of assembly. Secondly, it should be generally non-porous so that it excludes wet plaster from the air distributor layer 42 during formation of the cast layer 44. Third, it should possess an affinity for or a compatibility with the plaster so that a firm bond therewith can be established. A wide variety of materials are suitable for these purposes, an illustratively, dense jersey, canvas or any other relatively coarse woven material may be employed. Should there be utilized an air permeable material meeting the three noted requirements, there is obtained the added advantage of allowing force drying of the plaster cast from the interior thereof, thus effecting time and cost savings.

An exemplary sequence of steps in formation of the cast assembly C upon a body member M to the position shown in FIG. 1 will now be briefly described. The attending medical person first places the jersey sock 40 over the body part or member to be cast, allowing approximately four centimeters extra at each of the opposite ends of the sock. The porous load bearing air distribution layer 42 is then cut to fit around the body member M, over the jersey sock 40, but approximately seven centimeters back from the edges of the jersey material. The air distribution layer 42 is then secured in place with surgical tape or the like. The disposable snap socket assembly 20 with its protective cover 30 in a seated position is then located generally centrally on that area of the body member M to be cast and on top of the porous air distribution layer 42. It is secured in this position either by a pressure sensitive adhesive coating which has been applied thereto or by surgical tape.

The air chamber protector-plaster base layer 44 is next cut to cover the desired length to be cast. An opening in the layer 44 is cut of a size to allow the flange collar portion 26 of the snap socket assembly 20 to pass therethrough. The air chamber protector-plaster base layer 44 is then secured to the air distributor layer 42 either by its own pressure sensitive adhesive coating or by suitable surgical tape.

The ends of the jersey layer 40 are now folded back approximately four centimeters and over the layer 46, leaving the partially complete cast as thus formed at substantially its desired length.

The cast is then completed by molding thereon plaster of Paris in the conventional manner known to the art with care being taken to form the moldable plaster tightly around the body 22 and upper collar 26 of the snap socket assembly 20. At this time the protective cover 30 is of course in closed position upon the upper flange 26 of the socket assembly 20, and the plaster molded closely thereabout with care being taken so that at a later time, as when cast ventilation is being effected, the protective cover 30 can be easily raised, as to the position of FIG. 2.

When it is desired to utilize the cast assembly C of this invention in an operating mode the protective cover 30 is raised and the sealing connector assembly 12 located upon the socket assembly 20 in tight sealable relationship therewith. Air from the supply source A is then directed through the conduit means 10, passing through the manifold 38 and the connections 40 therefrom in the socket member 20, and the cast caused to be ventilated with conditioned air. In this manner, a gas such as air under the desired conditions of pressure, temperature and humidity is caused to flow along the inner working surfaces of the cast C, so that any excess heat and moisture is effectively driven from the interior of the cast along the surface of the patient's skin and discomfort, skin degeneration, swelling and other undesirable conditions avoided. These accomplishments are effected by use of a relatively light-weight cast structure which can be readily formed utilizing light-weight materials, and the desired air flow caused to take place from a portable air supply unit A operating at a very low noise level.

It will of course be appreciated that a number of casts worn by different patients may be connected to a single air supply A, and that particularly with a large cast more than a single socket member 20 may be embedded therein and by connector and conduit assemblies be connected to the air supply A. Also, upon occasion a small air pump may be provided hand operated by the patient or another person. Further, vacuum could be used in place of a positive displacement pump earlier discussed. In addition, it may at times be found expedient to establish communication between the air distributor layer 42 and the air supply A simply by inserting a connecting tubing into an opening in the cast assembly C.

Numerous changes and modifications to the invention have been set forth herein, and these and other variations may of course be effected without departing from the spirit of the invention or the scope of the subjoined claims.

What is claimed is:

1. A structural assembly providing a flow path for temperature and humidity controlled gas between a body member and a cast located thereon to effect ventilation therebetween, comprising a first relatively thick porous layer supported by a body member and providing a plurality of uninterrupted flow paths for randomly distributing gas flowing between said member and a cast located thereon, a second porous layer immediately adjacent said first layer providing a barrier against ingress of cast material during molding of said material to the body member; a passaged socket member adapted to be located in contact with said first and second porous layers for directing temperature and humidity controlled gas from a source through said first porous layer to effect ventilation between said body member and said cast; and a cover member adapted to be seated upon said socket member for directing gas from a source through said socket member and through said first porous layer at controlled temperature and humidity.

2. A structural assembly of the character defined in claim 1, in which the first porous layer is constructed of a relatively coarse woven material and also in which the second porous layer is of a relatively fine woven material.

3. A structural assembly of the character defined in claim 1, in which there is provided on said cover member and on said socket member complementary means for effecting sealing relation therebetween during movement of gas from a source through said cover and socket members and through said first porous layer to effect ventilation between said body member and said cast.

4. A structural assembly of the character defined in claim 1, in which said one of said woven layers is selected from the group consisting of jersey, canvas or like materials, and also in which said another of said woven layers is a plurality of superimposed plastic sheets.

5. A structural assembly of the character defined in claim 1, in which the passaged socket member is shaped to include flange means at opposite ends thereof whereby upon hardening of the cast material during molding to the body member contours said socket member is restrained against movement.

6. A structural assembly of the character defined in claim 1, in which the cover member on the underside thereof is provided with resiliently spreadable means engageable with the socket member surrounding the passage therein to effect a snap fit engagement therewith.

7. A structural assembly of the character defined in claim 1, in which there is provided an air source connected to the cover member and effective to control the temperature, pressure and humidity of the gas so as to supply conditioned gas to the first porous layer and effect ventilation between the cast and body member to reduce body discomfort.

8. A structural assembly adapted to be employed during immobilization of a body part by a cast of plaster of Paris or like material, which comprises a plurality of juxtaposed woven layers located between said body part and said plaster cast, one of said layers adjacent to said plaster cast being of relatively fine texture to provide a barrier against the passage therethrough of plaster material during the molding thereof and another of said layers adjacent to said body part being of relatively coarse texture and being of substantially greater thickness than said fine texture layer to permit the passage of temperature and humidity controlled air therethrough in substantially uninterrupted randomly directed flow paths to effect ventilation between said cast and said body part, and means connected to said cast and to a source of pressurized air for introducing air under positive pressure through said relatively coarse textured layer and between said body part and said cast to provide ventilation therebetween.

9. A structural assembly as defined in claim 8, in which the last-claimed means comprises a passaged socket member communicating with an air source and removably engageable with said socket member.

10. A method of reducing patient discomfort caused by immobilizing a body part with a cast formed of plaster of Paris or like material, which comprises surrounding the body part with a relatively thick layer of an air permeable loosely woven fibrous material, forming about the surrounded body part a plaster cast while maintaining a plurality of uninterrupted air flow passages therein from the air permeable layer to the exterior of the plaster cast, and introducing into the flow passages conditioned air controlled as to pressure, temperature and humidity to cause randomly directed air flow through the fibrous layer and along the adjacent body part to reduce patient discomfort occasioned by skin irritation and the like.

11. A method of reducing patient discomfort as defined in claim 1, in which subsequent to the surrounding step and prior to cast formation there is positioned upon the air permeable fibrous layer a layer of closely woven material providing a barrier against substantial passage of plaster material into the air permeable layer prior to formation of said material into rigid cast form.

12. A structural assembly as defined in claim 1, in which there is provided on the cover member and on the socket member cooperating means for effecting a snap fit connection therebetween while gas is flowing through the first porous layer to effect ventilation between the cast and body member.

* * * * *